United States Patent [19]

Forkner

[11] Patent Number: 4,838,247

[45] Date of Patent: Jun. 13, 1989

[54] DUAL-VIEW ARTHROSCOPE

[75] Inventor: John F. Forkner, Laguna Beach, Calif.

[73] Assignee: Baxter International, Inc., Deerfield, Ill.

[21] Appl. No.: 254,468

[22] Filed: Oct. 6, 1988

[51] Int. Cl.⁴ .............................................. A61B 1/06
[52] U.S. Cl. ..................................................... 128/6
[58] Field of Search .................................... 128/4, 6, 7

[56] References Cited

U.S. PATENT DOCUMENTS

| | | | |
|---|---|---|---|
| 2,987,960 | 6/1961 | Sheldon | 128/6 X |
| 3,901,220 | 8/1975 | Koyasu et al. | 128/6 |
| 3,918,438 | 11/1975 | Hayamizu et al. | 128/4 |
| 4,253,467 | 3/1981 | Frazier | 128/4 X |
| 4,398,811 | 8/1983 | Nishioka et al. | 128/7 X |
| 4,697,577 | 10/1987 | Forkner | 128/6 |
| 4,699,463 | 10/1987 | D'Amelio et al. | 128/4 X |

*Primary Examiner*—William H. Grieb
*Attorney, Agent, or Firm*—Gordon L. Peterson; Harry G. Weissenberger

[57] ABSTRACT

A rugged dual-view arthroscope construction is provided by encasing the optical train in an elongated channel or shoe which is pivotable within the barrel about the barrel axis. The axis of the optical train is offset from the barrel axis. A lens-and-prism assembly projects the image of a first field of view along the optical train axis in one pivotal position of the shoe, and the image of a second field of view along the optical train axis in another pivotal position of the shoe.

7 Claims, 2 Drawing Sheets

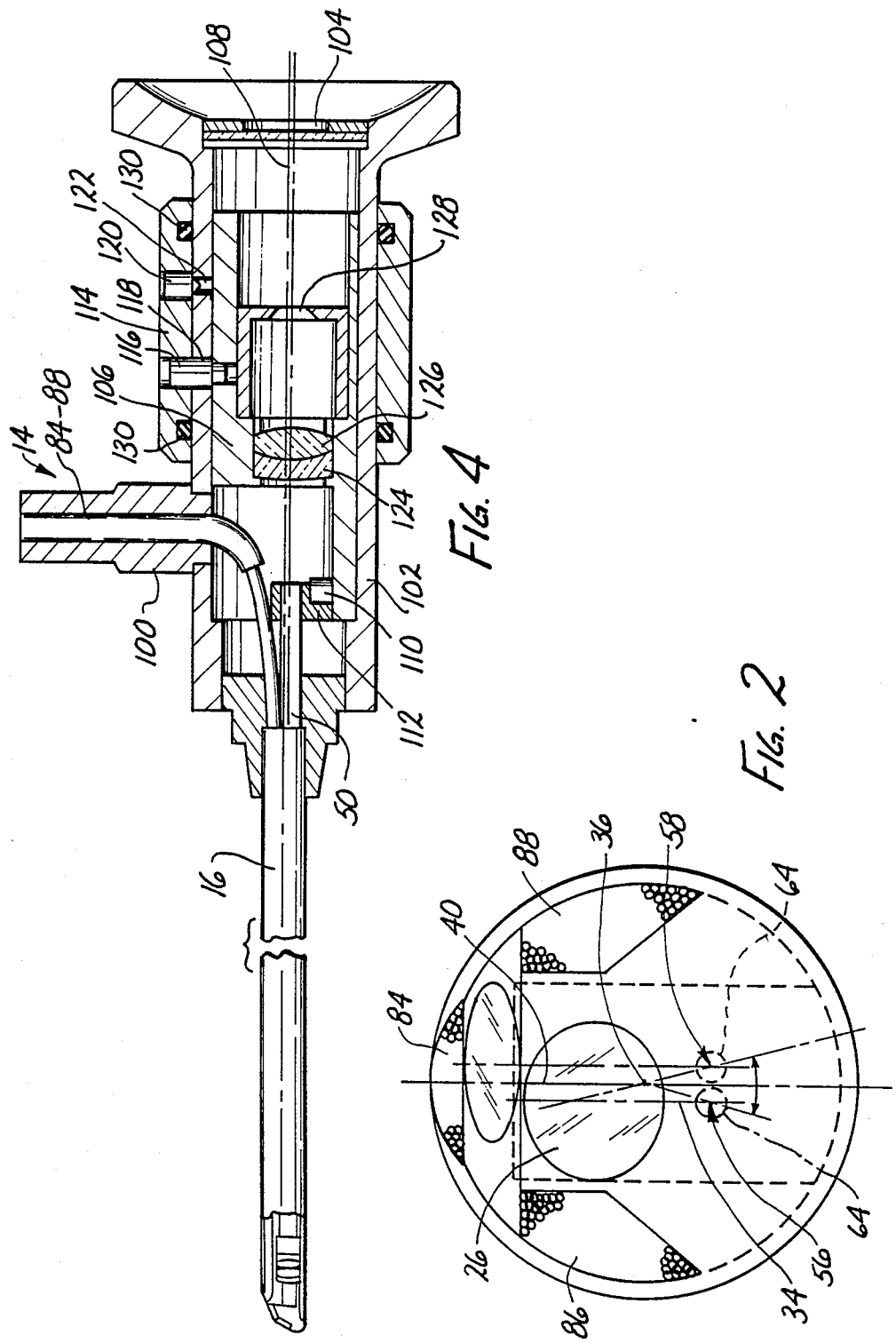

DUAL-VIEW ARTHROSCOPE

FIELD OF THE INVENTION

This invention relates to arthroscopes, and more particularly to a sturdy and highly reliable apparatus for changing the field-of-view angle.

BACKGROUND OF THE INVENTION

U.S. Pat. No. 4,697,577 discloses a dual-view arthroscope construction in which the field-of-view angle is changed by moving a lens prism transversely of the arthroscope axis between a silvered and an unsilvered surface of an objective prism. The lens prism is slidingly moved from side to side by a wire arrangement.

Although the apparatus of U.S. Pat. No. 4,697,577 works, the laterally sliding lens prism and the wire actuator are delicate mechanisms and present reliability problems due to the miniscule size of the parts involved. It therefore became necessary to devise an approach allowing a much more rugged construction.

SUMMARY OF THE INVENTION

The present invention provides a rugged actuating mechanism which is also optically superior, by encasing the optical train eccentrically in a generally U-shaped steel channel or shoe through an angle of about 30° whch is pivotable about the center of the semicircle formed by the bottom of the U. In the two extreme pivotal positions, the optical aperture in the front face of the shoe is opposite the pupil of the low-angle objective optics and the pupil of the high-angle objective optics, respectively.

The objective optics are composed of three fixed, mirrored prisms with associated lenses which work together to produce images of the low-angle and the high-angle field of view focused, respectively, at laterally spaced pupil locations which can be separately observed through the aperture of the shoe.

The shoe can be easily pivoted from the eyepiece end due to its inherent rigidity. At the eyepiece end, the resulting displacement of the optical train axis is followed by the eyepiece lens. Because the light emerging from the eyepiece lens is a collimated bundle, and the movement is very small, neither a human observer nor a camera at the eyepiece sees any shift or eclipsing of the image as the shoe is pivoted.

it is the object of the invention to provide a simple, rugged mechanism for giving an arthroscope dual-view capability.

It is another object of the invention to achieve that result by housing the optical train of the arthroscope eccentrically in a rigid, pivotable channel.

BRIEF DESCRIPTION OF THE DARWINGS

FIG. 2 is an end elevation of the objective end;

FIG. 4 is an axial vertical section through the eyepiece assembly of the arthroscope.

DESCRIPTION OF THE PREFERRED EMBODIMENT

Figure 1:
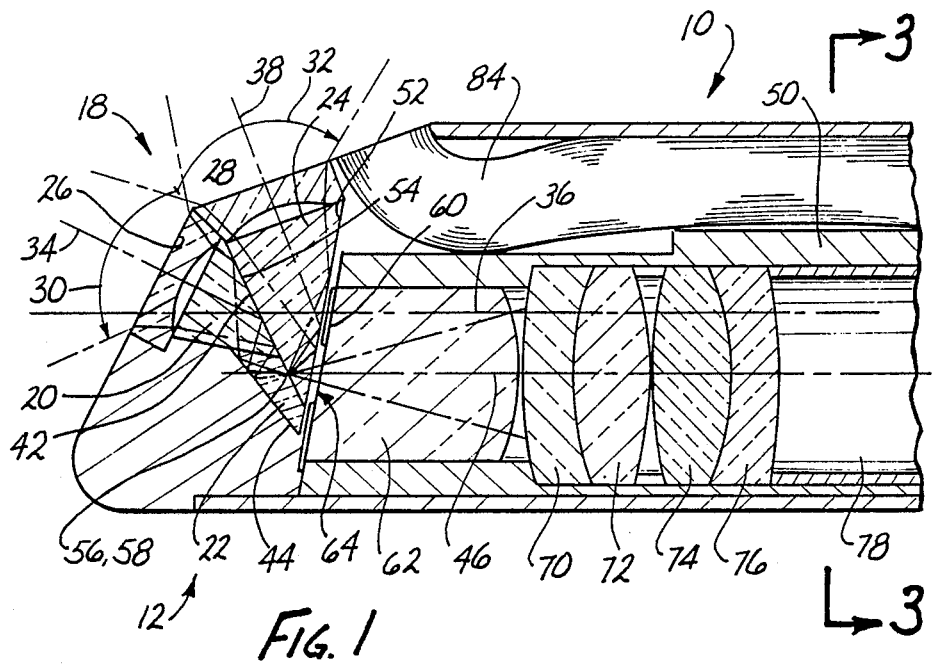
FIG. 1 is an axial vertical section through the objective assembly of the arthroscope of this invention.
Figure 3:
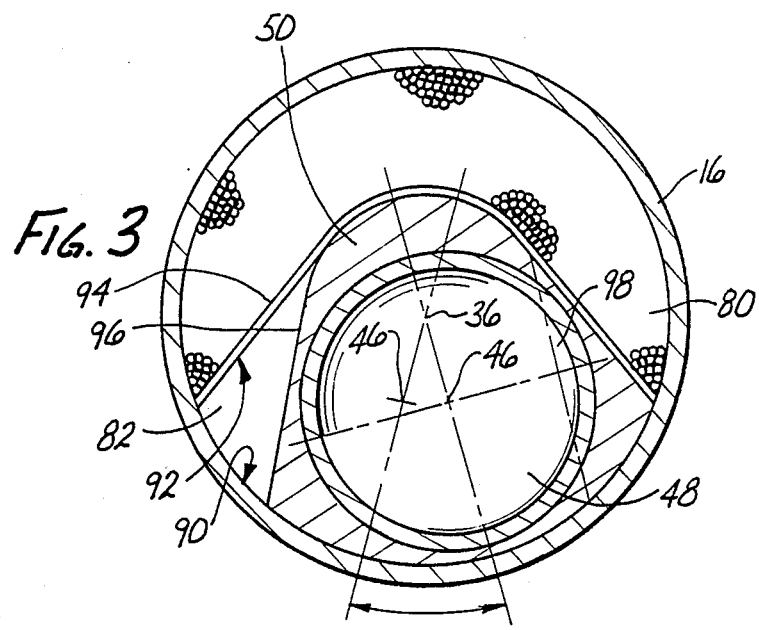
FIG. 3 is a transverse vertical section through the barrel of the arthroscope.

The arthroscope 10 of this invention is basically composed of an objective assembly 12 illustrated in detail in FIGS. 1 and 2, an eyepiece assembly 14 illustrated in detail in FIG. 4, and a rigid barrel 16, illustraed in detail in FIG. 3, containing the optical train and illumination fiber optics which opticaly interconnect the ojective and eyepiece.

As shown in FIG. 1, the objective assembly 12 contains fixed face optics 18 which include prisms 20, 22 and 24, as well as face lenses 26, 28 which define, respectively, a low-angle field of view 30 and a high-angle field of view 32. The axis 34 of the low-angle field 30 is preferably offset by about 27° from the axis 36 of the arthroscope 10, while the axis 38 of the high-angle field 32 is offset by about 70° from the axis 36. The face lenses 26, 28 each subtend a view angle of about 105°, so that the two face lenses between them cover a continuous field of view extending from about 25° below the axis 36 to about 122° above it.

As best seen in FIG. 2, the optical axes 34, 38 of face lenses 26, 28 are parallel to, but laterally displaced on opposite sides from a vertical plane 40 including the arthroscope axis 36. Referring back to FIG. 1, the center of the image seen by face lens 26 along the low-angle field's image axis 34 is reflected by the preferably fully mirrored surface 42 of prism 20. The image is then reflected a second time by the preferably fully mirrored surface 44 of prism 22. The orientations of the surfaces 42, 44 are such that the image axis 34 of the low-angle field 30 after the second reflection is coincident with the axis 46 of the optical train 48 (preferably a GRIN relay) in the low-angle position of the pivotable shoe 50 (dotted lines in FIG. 3).

Referring now again to FIG. 2, it will be noted that whereas the image axis 34 is positioned to the left of the plane 40 in FIG. 2, the image axis 38 of the high-ange field 32 is positioned to the right of the plane 40, and preferably at the same distance therefrom. Looking at FIG. 1, it will be seen that the high-angle image is reflected first by the surface 52 of prism 24, and then reflected a second time by the surface 54 of prism 24, which is mirrored only on the right side (in FIG. 2) of the plane 40. Following the second reflection, the image axis 38 is coincident with the optical train axis 46 in the high-angle position of shoe 50 (solid lines in FIG. 3).

The face lenses 26, 28 are so configured that the low-angle image is focused at the pupil 56 (FIG. 2) which is the intersection of the twice-reflected image axis 34 with the interface between prisms 22 and 24. Similarly, the once-reflected high-angle image is focused at the pupil 58 where its second reflection takes place.

Prisms 20, 22, 24 and face lenses 26, 28 are preferably cemented together to form the strong, unitary face optics 18. Because they are so cemented, the silvering of surfaces 42, 44 and 54 is necessary even though the prism material (LAF 21 is preferred) has a very high index of refraction. By contrast, surface 52 does not need to be silvered because an air gap exists between it and the surface 60 of the objective lens 62. An antireflective coating is probably privided on surface 52 to reduce light loss.

The surface 60 of objective lens 62 is opaqued, preferably by metallizing, except for a transparent circular objective aperture 64. A study of FIGS. 2 and 3 will show that in the low-angle position of shoe 50, the aperture 64 sees only the low-angle image emanating from pupil 56, while in the high-angle position of shoe 50, it sees only the high-angle image emanating from pupil 58.

The image seen by objective aperture 64 is collimated by the cemented doublet lenses 70, 72 and 74, 76. The collimated image is conveyed through an air space 78 to the face of the GRIN relay or other optical train 48 for transmission to the eyepiece 14 (FIG. 4) through the barrell 16 of the arthroscope 10. The axis 46 of the optical train 48 is displaced, as best shown in FIG. 3, with respect to the barrel axis 36 about which the shoe 50 pivots. Because of this offset, and because of the focusing of the images at the pupils 56, 58 which allows the aperture 64 to be made very small, it takes only about a 30° rotation of the shoe 50 to change the exposure of the optical train 48 from the low-angle image to the high-angle image.

As best seen in FIG. 3, the barrel 16 is divided into two lumens: the illumination lumen 80 and the optical lumen 82. The illumination lumen 80 contains the fiber optics conventionally used to convey light from an appropriate light source adjacent the eyepiece 14 through the barrel 16 to the face of the objective 12. In the objective 12, the fiber bundles contained in the lumen 80 divide into the high-angle illumination bundle 84 (FIG. 1) and a pair of low-angle illumination bundles 86, 88 visible only in FIG. 2.

The optical lumen 82 is defined by the inner surface 90 of the cylindrical barrel wall, and by the inner surface 92 of the divider wall 94. The surface 92 is cylindrical in its center and preferably flat at its sides. The surface 90 and the cylindrical portion of surface 92 have a common axis which coincides with the barrel axis 36. The shoe 50 is slidingly held between these surfaces and can thus be pivoted about the axis 36 between a low-angle position in which its side 96 contacts the surfce 92 (dotted lines in FIG. 3) and a high-angle position in which its side 98 contacts the surface 92 (solid lines in FIG. 3).

Turning now to FIG. 4, the eyepiece 14 is connected to the opposite end of barrel 16. The eyepiece 14 includes a fiber optic connector 100 at which the optical fiber strands 84, 86, 88 in the illumination lumen 80 of the barrel 16 can be connected to a conventional light source (not shown). The housing 102, on which the connector 100 is mounted, contains an observation window 104 and a lens carrier 106 which is rotatable about the axis 108 of the housing 102.

At its left end in FIG. 4, the lens carrier 106 carries a pin 110 which engages a shoe holder 112. The eypiece end of the shoe 50 is fixedly held in the holder 112 and is thereby pivoted about the barrel axis 36 (which coincides with the eyepiece housing axis 108) when the lens carrier 106 is rotated within the housing 102. The rotation of housing 102 is achieved by a collar 114. A pin 116 extending through an arcuate limiter slot 118 in the housing 108 operationally interconnects the collar 114 and lens carrier 106. A detent 120, by alternately engaging a pair of circumferentially spaced recesses 122 in the housing 108, holds the collar 114 in the low-angle or high-angle view position.

A cemented doublet eyepiece lens assembly 124, 126 projects the image emerging from the optical train 48 (FIG. 3) toward the observation window 104. It will be noted that the eypiece lens assembly is offset from the housing axis 108 and is instead centered on the optical train axis 46, so that it is always concentric with the optical train 48 as the arthroscope 10 is switched between the low-angle and the high-angle position.

As the image emerges from the lens assembly 124, 126, it is a collimated bundle projected through the aperture 128 toward the window 104. Consequently, its translation through the rather tiny arc between the low-angle and high-angle positions does not cause any image motion or eclipsing within the pupil of a human observer or a camera.

The collar 114 may be sealed in a conventional manner, as by O-rings 130, to allow sterilization of the arthroscope 10 without disassembly.

I claim:

1. A dual-view arthroscope, comprising:
   (a) as barrel having an axis;
   (b) a rigid, elongated channel disposed in said barrel for pivotal movement about said barrel axis between two limit positions;
   (c) an optical train mounted in said channel for movement therewith, said optical train having an axis spaced from but substantially parallel to said barrel axis; and
   (d) a face optics assembly so constructed as to project an image of a first field of view along said optical train axis when said channel is in one of said limit positions, and an image of a second field of view along said optical train axis when said channel is in the other of said limit positions.

2. The arthroscope of claim 1, in which said face optics assembly includes:
   (i) a pair of face lenses adapted to focus said images, said lenses being disposed at different angles to said barrel axis and centered on opposite sides of a plane including said barrel axis; and
   (ii) a set of prisms assocaited with said face lenses and arranged to reflect said images respectively to a pair of focal points spaced from said barrel axis but equidistant therefrom.

3. The arthroscope of claim 2, in which said prism set includes a pair of prisms juxtaposed in such a manner that said focal points are located on the interface between said pair of prisms, said interface being reflective at one of said focal points and transparent at the other.

4. The arthroscope of claim 1, in which said barrel has a pair of arcuate surfaces each centered on said barrel axis, and said channel is in the form of a shoe slidable along said arcuate surfaces for pivotal movement about said barrel axis.

5. The arthroscope of claim 1, further comprising:
   (e) an eyepiece attached to said barrel, said eyepiece including a housing having an axis coincident with said barrel axis;
   (f) an eyepiece lens assembly mounted in said housing for rotational movement about said housing axis, said eyepiece lens assembly having an axis substantially parallel to but spaced from said housing axis;
   (g) means for rotating said eyepece lens assembly; and
   (h) means for operationally interconnecting said eyepiece lens assembly and said channel in such a manner as to maintain said lens assembly axis coincident with said optical train axis.

6. The arthroscope of claim 5, in which said eyepiece lens assembly collimates the image transmitted by said optical train.

7. The arthroscope of claim 6, said eyepiece further comprising window means for observing said collimated image.

* * * * *

UNITED STATES PATENT AND TRADEMARK OFFICE
CERTIFICATE OF CORRECTION

PATENT NO. : 4,838,247
DATED : June 13, 1989
INVENTOR(S) : John F. Forkner

It is certified that error appears in the above-identified patent and that said Letters Patent is hereby corrected as shown below:

Column 1, line 28 change "whch" to -- which --.

Column 1, line 48 change "it" to -- It --.

Column 2, line 3 change "ojective" to -- objective --.

Column 2, line 34 change "high-ange" to -- high-angle --.

Column 2, line 59 change "privided" to -- provided --.

Column 4, line 33 change "assocaited" to -- associated --.

Column 4, line 55 change "eyepece" to -- eyepiece --.

Signed and Sealed this

Tenth Day of July, 1990

Attest:

HARRY F. MANBECK, JR.

*Attesting Officer*

*Commissioner of Patents and Trademarks*